United States Patent [19]
Yang

[11] Patent Number: 5,275,704
[45] Date of Patent: Jan. 4, 1994

[54] METHOD AND APPARATUS FOR MEASURING UNDERDEPOSIT LOCALIZED CORROSION RATE OR METAL CORROSION RATE UNDER TUBERCLES IN COOLING WATER SYSTEMS

[75] Inventor: Bo Yang, Naperville, Ill.

[73] Assignee: Nalco Chemical Company, Naperville, Ill.

[21] Appl. No.: 961,641

[22] Filed: Oct. 16, 1992

[51] Int. Cl.$^5$ .............................................. G01N 27/26
[52] U.S. Cl. ................. 204/153.11; 204/404
[58] Field of Search .......................... 204/153.11, 404; 324/425, 700, 71.2

[56] References Cited
U.S. PATENT DOCUMENTS

| | | | |
|---|---|---|---|
| 3,660,249 | 5/1972 | Townsend | 204/153.11 |
| 3,878,064 | 4/1975 | Weisstuch et al. | 204/153.11 |
| 4,395,318 | 7/1983 | Tait et al. | 204/404 |
| 4,994,159 | 2/1991 | Agarwaza et al. | 204/153.1 |
| 5,045,775 | 9/1991 | White et al. | 324/71.2 |

*Primary Examiner*—Aaron Weisstuch
*Attorney, Agent, or Firm*—Robert A. Miller; Joseph B. Barrett; James J. Drake

[57] ABSTRACT

A method and apparatus is provided for measuring underdeposit localized corrosion rate of a metal structure under differential flow conditions encountered in actual cooling water systems. A first electrode defining a slow flow electrode is immersed in an electrolytic liquid. A second electrode defining a fast flow electrode is also immersed in the electrolytic liquid. Different fluid dynamic conditions are created on the slow flow and fast flow electrodes. There are three (3) techniques for obtaining measurement from a differential flow cell so as to determine the underdeposit localized corrosion rate due to differential flow conditions. In one embodiment, the different fluid dynamic conditions are created by rotating the slow flow electrode at a first speed and by rotating the fast flow electrode at a second speed which is higher than the first speed.

18 Claims, 3 Drawing Sheets

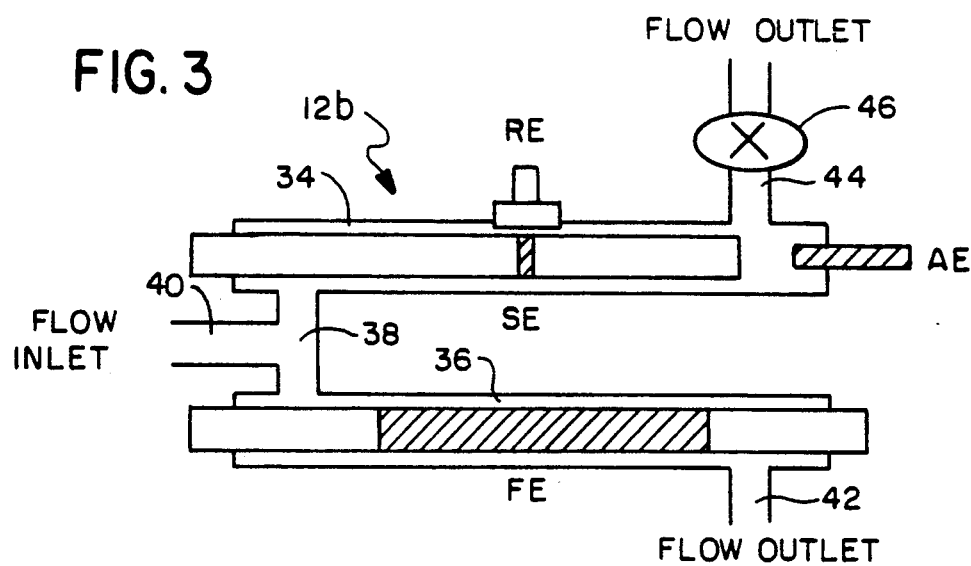
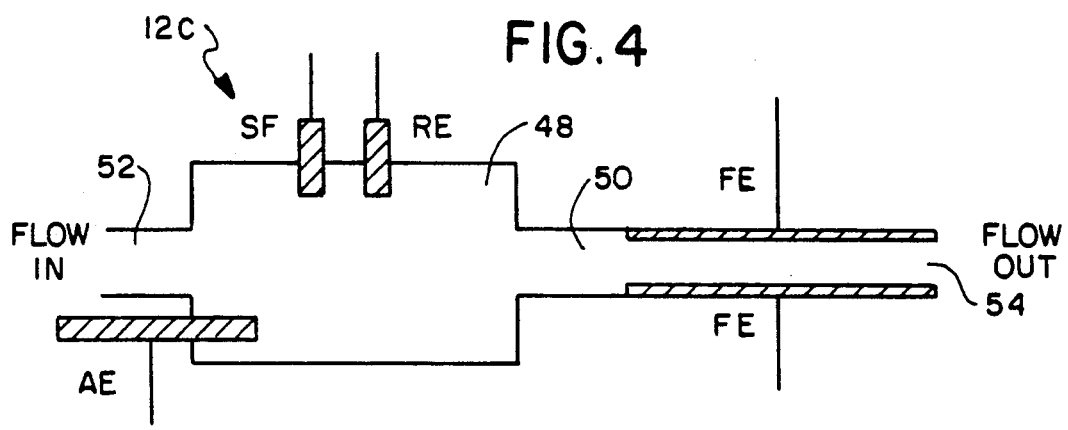
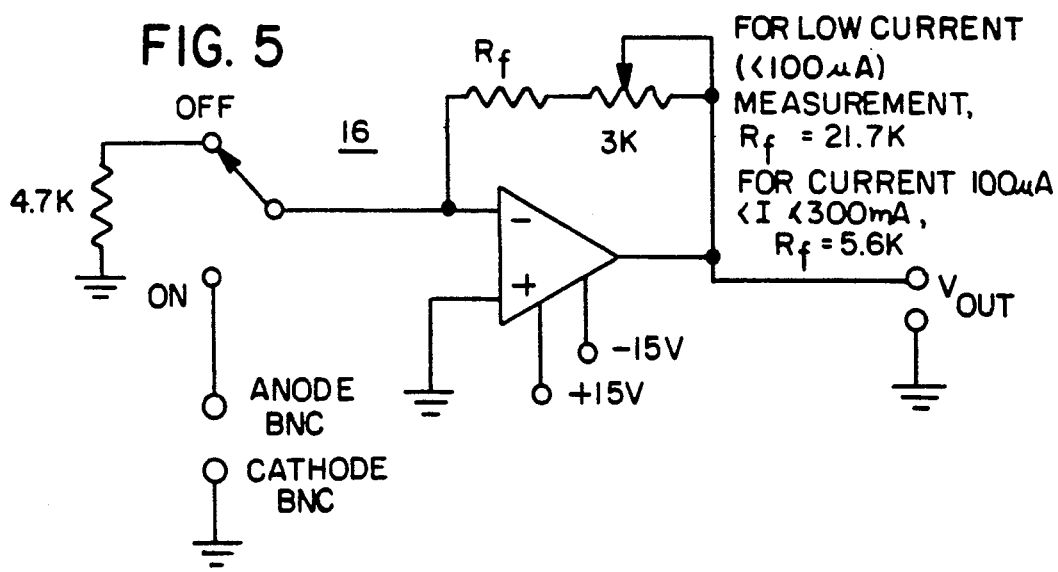

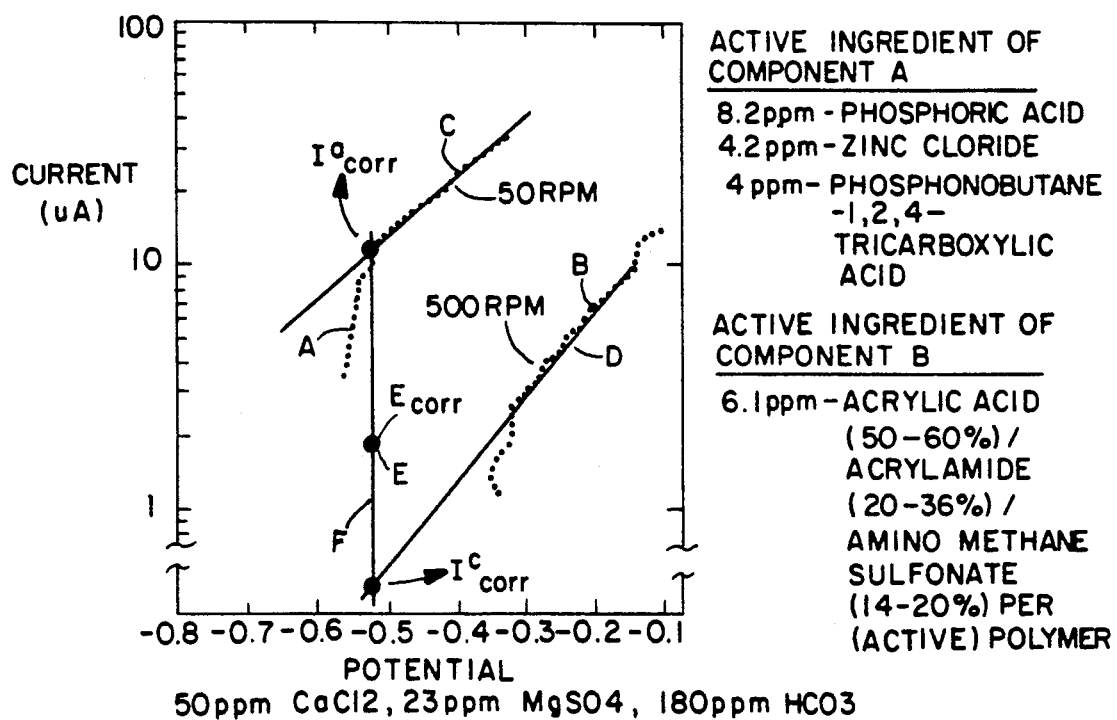
FIG.6
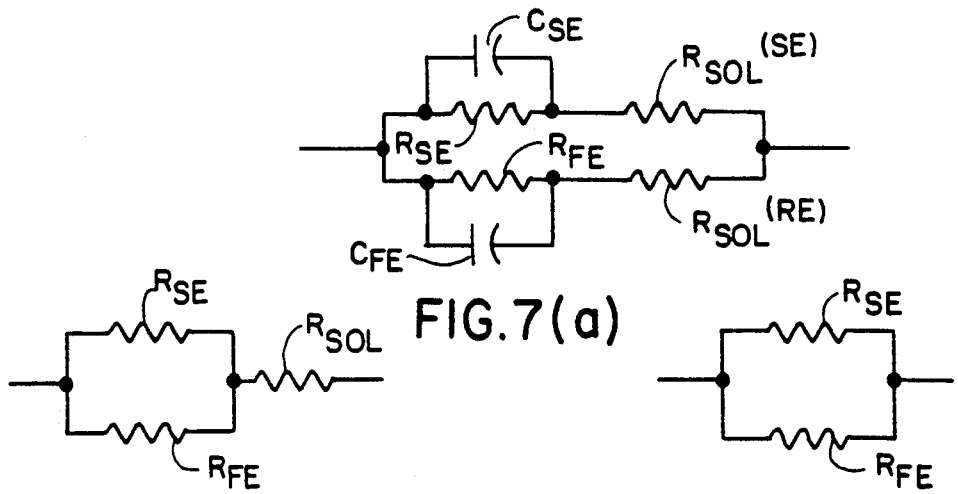
FIG.7(a)
FIG.7(b)
FIG.7(c)

METHOD AND APPARATUS FOR MEASURING UNDERDEPOSIT LOCALIZED CORROSION RATE OR METAL CORROSION RATE UNDER TUBERCLES IN COOLING WATER SYSTEMS

BACKGROUND OF THE INVENTION

1. Field of the Invention

This invention relates generally to corrosion monitoring and measuring apparatuses and more particularly, it relates to a method and apparatus for monitoring reliably and realistically the localized corrosion rate of metals exposed to an aerated electrolytically conductive liquid environment. In particular, the present invention is directed to a method and apparatus for measuring underdeposit corrosion rate or metal corrosion rate under tubercles in cooling water systems.

2. Description of the Prior Art

As is generally known in industrial and commercial systems having a metal part which comes in contact with an electrolytic fluid, a major problem is localized corrosion, for instance pitting or crevice attack, because such corrosion will occur intensely in one particular location and may cause perforations in the structural member carrying the electrolytic fluid. Obviously, these perforations may cause leaks which require shutting down of the entire industrial system so that repairs can be made. As a result, the useful life of the structural member will be shortened. Pitting/localized corrosion is typically far more of a concern than general corrosion since general corrosion occurs essentially at a constant rate over an entire surface and will not cause a potentially dangerous leak in a short period of time as in the case of localized corrosion.

Therefore, there has arisen a need for corrosion monitoring systems for the purpose of estimating the residual service life of the structural member. Further, in industrial systems for cooling water treatment application there is an urgent demand for monitoring effectively and realistically the performance of a given chemical treatment program for controlling localized corrosion.

There are known in the prior art various corrosion monitoring apparatuses for determining general and/or localized corrosion rates. For example, in U.S. Pat. No. 3,660,249 issued on May 2, 1972, to C. R. Townsend, there is disclosed a method and apparatus for determining both the general or average corrosion rate and the pitting tendency of a metal exposed to an electrolyte which utilizes a corroding electrode, a reference electrode, and an auxiliary electrode. The corroding electrode is made 10 mv positive relative to the reference electrode and is then made 10 mv negative relative thereto. The anodic and cathodic currents which flow through a circuit including the corroding electrode and the auxiliary electrode are then averaged to produce an indication of the general or average corrosion rate. The difference between such anodic and cathodic currents is determined in order to provide the pitting tendency or pitting index of the system.

In U.S. Pat. No. 3,878,064 issued on Apr. 15, 1975, to A. Weisstuch and C. E. Schell III, there is disclosed a method and apparatus for measuring pitting corrosion tendencies of metals exposed to an electrolytic liquid which has a Cathode, an Anode, a Reference Electrode, and an Auxiliary Electrode positioned in the electrolytic liquid. The open circuit potential between the Cathode and Reference Electrode is impressed upon a capacitor. By means of a two-position switch, an operational amplifier then causes the potential of the Anode, in a circuit including the Reference Electrode, Auxiliary Electrode (or the electrode previously used as the Cathode) and an Ammeter, to be equal to the open circuit cathode-reference electrode potential. The amplifier provides the necessary current of either polarity so as to achieve this equality. The polarization current flowing through the Ammeter is read and a qualitative indication of the pitting tendency is obtained.

U.S. Pat. No. 4,575,678 issued on Mar. 11, 1986, to K. Hladky teaches a corrosion monitoring apparatus for monitoring the corrosion of a metal part which includes the part defining a first electrode in contact with an electrolyte and a second electrode in contact with the electrolyte but electrically insulated from the first electrode. A high input impedance voltmeter is connected across the first and second electrodes. The low frequency voltage between the electrodes is observed. This voltage is a low frequency noise signal. The amplitude values of the signal are measured and subjected to an averaging computation yielding data indicating the corrosion rate of the first electrode and the nature of the corrosion.

U.S Pat. No. 5,045,775 issued on Sept. 3, 1991, to M. L. White and H. Leidheiser, Jr. teaches a system for monitoring and measuring the corrosion reaction of metals in an environment. The system includes a sample corrosion element of substantially the same material as the structure to be monitored, a galvanic cell for generating an electric signal indicative of the corrosion on the corrosion element, and a monitor for receiving and storing the generated signal. The system is designed to incorporate corrosion products and environmental contaminants in order to simulate actual, localized conditions on a particular area of a civil engineering structure exposed to atmospheric corrosion.

PCT application No. WO 87/07022 filed May 11, 1987, to D. A. Eden et al. describes a method and apparatus for detecting and measuring localized corrosion of a metal surface which includes an array of electrodes fabricated from the same material as the metallic surface and exposed to the same corrosion conditions as the metallic surface. The coupling current between the array of electrodes is measured, and the electrochemical current noise originating in the electrode array is measured. The two measurements are compared to provide an output indicative of the degree to which corrosion is localized. Further, the apparatus also includes means for providing a resistive/impedance noise related output based upon an electrochemical potential noise and the electrochemical current noise. The output indicative of the degree to which corrosion is localized and the resistive/impedance noise output are compared to provide a second output indicative of the rate of localized corrosion.

However, all of the prior art corrosion monitoring systems discussed have their drawbacks and none of them can provide realistic and effective monitoring of localized corrosion. It has been realized by previous experience that it is of critical importance to have the capability of monitoring both the initialization and the propagation stages of localized corrosion. Further, earlier studies have established that all of the cooling water treatment programs (i.e., stabilized phosphate, zinc containing programs, and alkaline phosphate programs) achieve their corrosion protection function by forming a compact layer of inhibitors on the metal surface in the formation process and thus the protective quality of the film depends on fluid dynamic conditions.

By realizing that the existence of different fluid dynamic conditions is an inherent property of any actual cooling water system, the inventor has developed a method and apparatus for measuring underdeposit localized corrosion rate of carbon steel and cast iron structures under differential flow conditions encountered in actual cooling water systems. This apparatus allows for the capability of evaluating a chemical treatment program against the initialization and the propagation of underdeposit localized corrosion.

SUMMARY OF THE INVENTION

Accordingly, it is a general object of the present invention to provide a method and apparatus for monitoring reliably and realistically localized corrosion rate of metals exposed to an aerated electrolytically conductive liquid environment.

It is an object of the present invention to provide a method and apparatus for measuring underdeposit corrosion rate or metal corrosion rate under tubercles in cooling water systems.

It is another object of the present invention to provide a method and apparatus for measuring underdeposit localized corrosion rate of carbon steel and cast iron structures under differential flow conditions encountered in actual cooling water systems.

It is still another object of the present invention to provide a method and apparatus which allows for the capability of evaluating a chemical treatment program against the initialization and the propagation of underdeposit localized corrosion.

In accordance with a preferred embodiment of the present invention, there is provided a method and apparatus for measuring underdeposit localized corrosion rate of a metal structure under differential flow conditions encountered in actual cooling water systems. A first electrode defining a slow flow electrode is placed in an electrolytic liquid. A second electrode defining a fast flow electrode is also placed in the electrolytic liquid. Different fluid dynamic conditions are created on the slow flow and fast flow electrodes.

In one preferred technique, a current flowing between the slow flow and fast flow electrodes is measured. A current flowing between the slow flow electrode separately and an auxiliary electrode under a small polarization potential around the slow flow electrode corrosion potential is then measured to determine a first polarization resistance. The current flowing between the slow flow and fast flow electrodes and the first polarization resistance are utilized to determine the underdeposit localized corrosion rate due to differential flow conditions.

In another preferred technique, the slow and fast flow electrodes are shorted together, and the current flowing between an auxiliary electrode and the shorted slow flow and fast flow electrodes under a small applied potential around its corrosion potential is measured to determine a first polarization resistance. A current flowing between the fast flow electrode separately and the auxiliary electrode under a small polarization potential around the fast flow electrode corrosion potential is then measured to determine a second polarization resistance. The first and second polarization resistances are utilized to produce a third polarization resistance associated with the slow flow electrode which is used to determine the underdeposit localized corrosion rate due to differential flow conditions.

BRIEF DESCRIPTION OF THE DRAWINGS

These and other objects and advantages of the present invention will become more fully apparent from the following detailed description when read in conjunction with the accompanying drawings with like reference numerals indicating corresponding parts throughout, wherein:

FIG. 3 is a diagrammatical representation, illustrating an alternative embodiment for creating a differential flow cell;

FIG. 4 is a diagrammatical representation, illustrating another alternative embodiment for creating a differential flow cell;

FIG. 5 is a schematic circuit diagram of a zero-resistance ammeter for use in FIGS. 1 and 2;

FIG. 6 shows how a first method is used for determining corrosion rates in the differential flow cell of FIG. 1; and FIGS. 7(a)-7(c) are equivalent electrical circuits for the differential flow cell of FIG. 1.

DESCRIPTION OF THE PREFERRED EMBODIMENTS

Figure 1:
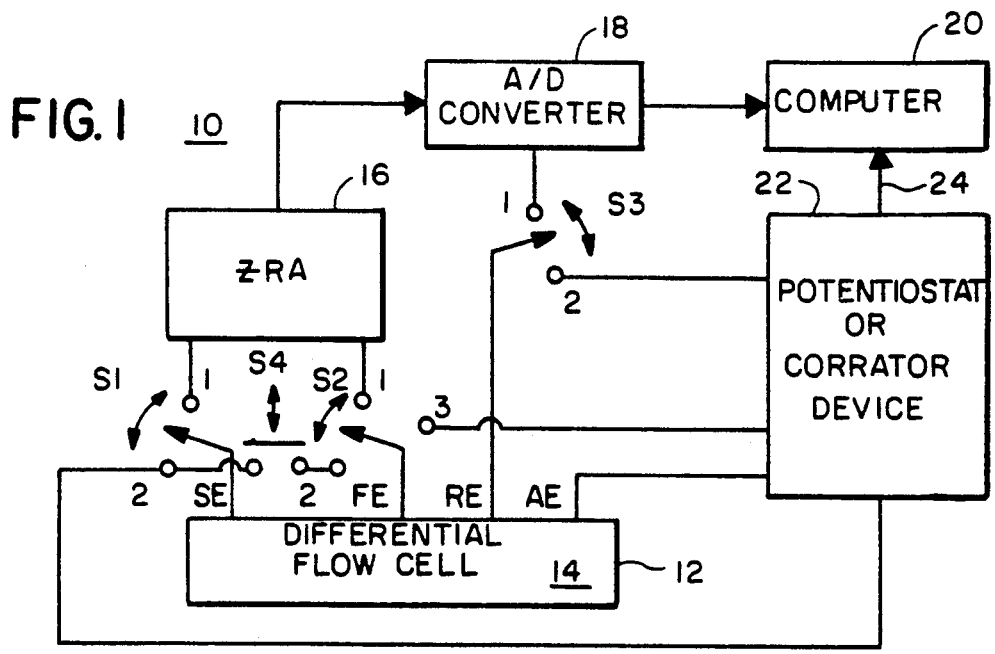
FIG. 1 is a block diagram of an apparatus of the present invention, illustrating the measurements performed on a differential flow cell.

Referring now in detail to the drawings, there is shown in FIG. 1 a block diagram of an apparatus 10 of the present invention for measuring underdeposit localized corrosion rate of a metal structure, such as carbon steel or cast iron, under differential flow conditions encountered in actual cooling water systems. The apparatus 10 permits the capability of evaluating a chemical treatment program against the initialization and the propagation stages of localized corrosion under tubercles. The apparatus allows for the determination of underdeposit corrosion rate as a function of time and changing operating conditions. Further, the apparatus can also provide information on whether the non-corroded area will contribute to the corrosion of localized sites and produce an estimate of the extent of such contribution.

The apparatus 10 includes a solution container 12 which contains an electrolytic liquid 14 therein. It should be understood that the solution container may be a variety of liquid containing means such as a pipe, conduit, a storage tank, or process vessel in which different fluid dynamic conditions can be created, as will be explained more fully hereinafter. A first or slow flow electrode SE is referred to as an anode and is positioned in the electrolytic liquid 14. The second or fast flow electrode FE is referred to as a cathode and is also positioned in the electrolytic liquid at a spaced apart distance from the slow flow electrode SE. The slow flow and fast flow electrodes are usually made of the same material and are fabricated from the same material as the metal structure, i.e., mild steel.

The slow flow electrode SE is preferably formed of a much smaller surface area than the fast flow electrode FE. Generally, the area ratio of the fast-to-slow electrodes should be larger than ten. Further, the slow flow electrode is preferably formed of a surface area of less than one sq. cm. A reference electrode RE and an optional auxiliary electrode AE are also positioned in the electrolytic liquid 14. The reference electrode RE is generally placed close to the slow flow electrode SE. The reference electrode RE is preferably made of SCE (saturated calomel electrode) or Ag/AgCl. The auxiliary electrode AE is preferably made of graphite.

In some instances, the auxiliary electrode AE and the reference electrode RE can be merged into a single electrode, especially in cases where a reading of the accurate absolute value of the corrosion potential is not required. In these cases, the single electrode AE/RE can be made of a mild steel or platinum.

It is also worthwhile to point out that, in principle, by varying the fast flow (cathode)/slow flow (anode) area ratio the resulting steady state corrosion rate of the slow flow electrode (anode) should be a good representation of the steady state penetration rate of any kind of localized corrosions in cooling water systems, regardless of whether the localized attack has originated from pitting (corresponding to a large cathode/anode ratio) or from the accumulation of loose deposits. This is because that under such conditions the tubercles covering the corroded site will have a similar composition as the one in the differential flow cell anode.

Earlier studies have established that under operating conditions used in cooling water systems (i.e., in systems where controlling corrosion is achieved through the use of phosphate containing programs, zinc containing programs, or all-organic programs, for instance, programs containing organic phosphonates), the inhibitor film formation at the slow flow electrode is usually slower than at the fast flow electrode. In addition, the film thus formed is also less protective and usually porous. Because of these existing factors, the slow flow electrode will undergo preferential corrosion in comparison with the fast flow electrode. As the immersion time increases, the slow flow electrode (anode) will be covered with tubercles (a loose deposit layer) consisting of a mixture of iron oxides, iron hydroxides, as well as co-deposits of other solution constituents. From then on, the mechanisms of differential aeration, restricted solution exchange, and mass transfer which are operative in underdeposit localized corrosion phenomena will become dominant and dictate the extent of corrosion attack on the slow flow electrode.

There are three (3) techniques or methods that can be used to determine the corrosion rates at the slow flow electrode SE and at the fast flow electrode FE that are based upon measurements performed on the solution container 12 which is used to create a differential flow cell. The first method can be referred to as the Tafel extrapolation method. This method is based upon the extrapolation of the log (i) vs. potential E linear region of the anodic branches of the polarization curves of the anode and cathode electrodes to the corrosion potential $E_{corr}$ of the system.

With the switches S1 and S3 turned to position No. 2 in FIG. 1, the voltage of the potentiostat 22 is incrementally varied between 0-250 mv vs. $E_{corr}$, and the corresponding current readings are taken and are plotted to obtain the curve A as shown in FIG. 6. This curve A represents the anodic branch (iron dissolution) of the polarization curve of the slow flow electrode SE. Then, with the switches S2 and S3 turned to position No. 2 in FIG. 1, the voltage of the potentiostat 22 is again incrementally varied between 0-250 mv vs. $E_{corr}$, and the corresponding current readings are taken and are plotted to obtain the curve B as shown in FIG. 6. This curve B represents the anodic branch (iron dissolution) of the polarization curve of the fast flow electrode FE. It will be noted that these current readings can be fed to a computer 20 via line 24 for processing and storage.

By extrapolating the curves A and B, there are obtained the straight lines C and D, respectively. Finally, with the switches S1-S3 turned to position No. 2 and the switch S4 being depressed so as to short the slow flow and fast flow electrodes together, the corrosion potential $E_{corr}$ is measured and is plotted at point E on FIG. 6. By extending a vertical line F through the point E until it intersects the lines C and D, there are obtained corrosion currents or corrosion rates $I^a_{corr}$ and $I^c_{corr}$ at the anode and cathode, respectively.

This corrosion current $I^c_{corr}$ at the cathode provides information on the extent of the general corrosion rate. Since the slow flow electrode is usually covered with tubercle-like deposits, this corrosion current $I^a_{corr}$ at the anode provides information corresponding to the underdeposit localized corrosion rate. Therefore, it can be seen that these measurements obtained from the differential flow cell provides information on both the initialization and the propagation of localized corrosion between the anode and the cathode. Obviously, the anode corrosion rate at the initial stage of immersion and the magnitude of the current flowing between the anode and the cathode indicate the tendency of initialization of localized corrosion while the steady state corrosion rate of the anode provides a quantitative measure of the propagation rate of the localized corrosion.

When the solution ohmic drop is sufficiently small (i.e., the solution conductivity is high) or is properly accounted for, this first method yields an accurate reading of the corrosion rates. While this method provides accurate corrosion rate readings, it has the disadvantage of requiring the use of sophisticated equipment (i.e., the potentiostat).

The second technique or method is based upon (1) the polarization resistance associated with the slow flow electrode separately, (2) the polarization resistance associated with the fast flow electrode separately, and (3) the polarization resistance of the anode and cathode electrodes connected together so as to yield the corrosion rates. Initially, it is assumed that the differential flow cell of FIG. 1 can be represented by an equivalent electrical circuit as shown in FIG. 7(a). The resistor $R_{se}$ is the polarization resistance of the slow flow electrode, which is inversely proportional to the corrosion rate at the anode. The resistor $R_{fe}$ is the polarization resistance of the fast flow electrode, which is inversely proportional to the corrosion rate at the cathode. The capacitors $C_{se}$ and $C_{fe}$ represent the electrical double layer capacitances of the slow flow and fast flow electrodes, respectively. The series resistors $R_{sol(se)}$ and $R_{sol(fe)}$ represent the solution ohmic drops associated with respective slow flow and fast flow electrodes.

When the measurements performed on the differential flow cell use only DC currents and are conducted at steady state conditions, the effects of the capacitances represented by the slow flow capacitor $C_{se}$ and the fast flow capacitor $C_{fe}$ are negligible. Thus, the equivalent circuit of FIG. 7(a) can be simplified and is shown in FIG. 7(b). As can be seen, the slow flow polarization resistance $R_{se}$ and the fast flow polarization resistance $R_{fe}$ are connected in a parallel arrangement which is further connected in series with resistor $R_{sol}$. The resistor $R_{sol}$ represents the total solution ohmic drop associated with the slow flow and fast flow electrodes.

When the total solution ohmic drop $R_{sol}$ is negligible (solution conductivity is high) or is corrected in the measurements performed, the equivalent circuit of FIG. 7(b) can be further simplified and is shown in FIG. 7(c). It will be noted that the differential flow cell is represented by the parallel combination of the slow flow polarization resistance $R_{se}$ and the fast flow polarization resistance $R_{fe}$. Thus, the measured polarization resistance $R_t$ obtained when the slow flow electrode and the fast flow electrode are connected together is given by the following equation:

$$R_t = R_{se} \cdot R_{fe}/(R_{se} + R_{fe}) \quad (1)$$

By solving the above equation (1) for the slow flow polarization resistance $R_{se}$, there is given:

$$R_{se} = R_t \cdot R_{fe}/(R_{fe} - R_t) \quad (2)$$

With the switches S1–S3 in FIG. 1 turned to position No. 2 and the switch S4 being depressed so as to short the slow flow and fast flow electrodes together, a Corrator-like device 22 with the use of the reference electrode, which is a less sophisticated device than the potentiostat, can be used to apply a small fixed overvoltage (i.e., 10 mv) across the shorted slow and fast flow electrodes and the auxiliary electrode and the corresponding current flowing therein is read. The voltage and the current reading are processed by the computer 20 via the line 24 to determine the polarization resistance $R_t$ of equation (2).

When the surface area $A_{fe}$ of the fast flow electrode FE is much larger than the surface area $A_{se}$ of the slow flow electrode SE, the polarization resistance $R_{fe(i)}$ of the fast flow electrode measured when the slow flow electrode is disconnected is assumed to be the same value of the resistor $R_{fe}$ in FIG. 7(c). It is generally preferred that the surface area $A_{fe}$ be at least ten times greater than the surface area $A_{se}$. Further, it is most preferred that the surface area $A_{fe}$ be approximately 30–40 times greater than the surface area $A_{se}$ so as to provide a more accurate measurement.

Therefore, the value of the resistor $R_{fe}$ can be measured by turning the switch S3 to position No. 2 and switch S2 to position No. 3 in FIG. 1. Then, the Corrator-like device 22 with the use of the reference electrode is again used to apply a small fixed overvoltage across the fast flow electrode and the auxiliary electrode and the corresponding current flowing is read. The voltage and the current reading are processed by the computer to determine the fast flow polarization resistance $R_{fe}$ (cathodic current) of equation (2). This polarization resistance $R_{fe}$ provides information on the extent of general corrosion rates.

Thus, the corrosion rate $CR^c_{corr}$ of the fast flow electrode is given by:

$$CR^c_{corr}(mpy) = k/(A_{fe} \cdot R_{fe}) \quad (3)$$

Further, the corrosion rate $CR^a_{corr}$ of the slow flow electrode is given by:

$$CR^a_{corr}(mpy) = K/(A_{se} \cdot R_{se}) \quad (4)$$

where $R_{se}$ is determined from above equation (2)

The value of K is a constant. The specific value of K is a function of the Tafel slopes, the density of the metal, and the equivalent weight of the metal.

Finally, the third technique or method is based upon (1) the current $I_{(short)}$ flowing between the slow flow electrode and the fast flow electrode, and (2) the polarization resistance $R_{se(i)}$ of the slow flow electrode measured when the fast flow electrode is disconnected so as to obtain the corrosion rate of the slow flow electrode (i.e., underdeposit corrosion rate). Thus, the underdeposit corrosion rate $CR^a_{corr}$ of the slow flow electrode can be expressed mathematically as follows:

$$CR^a_{corr}(mpy) = (I_{(short)} \cdot 0.46)/A_{se} + K/(A_{se} \cdot R_{se(i)}) \quad (5)$$

The value of K is a constant and has the same meaning as in the second method. The unit of the current $I_{(short)}$ is uA. When the unit of the polarization resistance $R_{se(i)}$ is kohms·cm², then the value of the constant K is approximately between 10 to 35. The first term of equation (5) represents the contribution of the cathodic reaction (usually oxygen reduction) occurring in the cathode towards the corrosion of the anode. The second term of equation (5) represents the contribution of oxygen reduction occurring on the anode itself towards its own corrosion.

Therefore, the value of the current $I_{(short)}$ in the first term of equation (5) can be measured by turning the switches S1–S3 in FIG. 1 to position No. 1. It can be seen that a zero-resistance ammeter 16 will be connected across the slow flow electrode SE (anode) and the fast flow electrode FE (cathode). A high current reading as measured by the ammeter 16 indicates a high localized corrosion rate. This current reading, which is an analog signal, is fed to an A/D converter 18 so as to be processed and stored by the computer 20. A schematic circuit diagram of the zero-resistance ammeter 16 is shown in FIG. 5 of the drawings.

In order to obtain the value of $R_{se(i)}$ in the second term of equation (5), the switches S1 and S3 are turned to position No. 2 and the Corrator-like device 22 with the use of the reference electrode is once again used to apply a small fixed overvoltage across the slow flow electrode and the auxiliary electrode and the corresponding current flowing is read. The voltage and the current reading are processed by the computer 22 to determine the slow flow polarization resistance $R_{se(i)}$.

Therefore, a chemical water treatment program can be evaluated to determine whether adequate protection for the metal structure (i.e., steel) against underdeposit localized corrosion based upon the measurements obtained by any of the three (3) methods described above from the differential flow cell. The higher polarization resistance values and the lower current values indicate the better the program performs on providing protection against underdeposit corrosion due to differential flow conditions. However, the second and third techniques for determining the corrosion rates are more preferred than the first method since it requires the use of sophisticated equipment, as previously pointed out.

Figure 2:
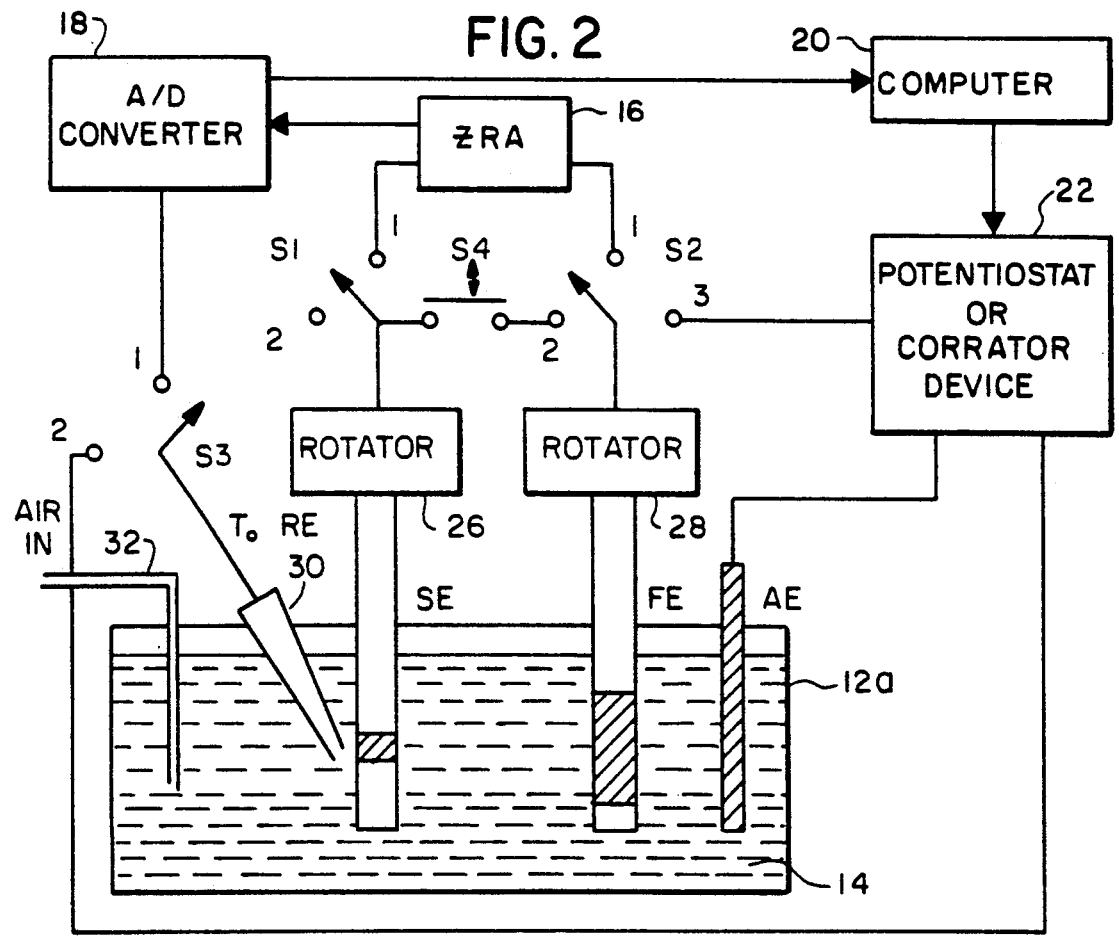
FIG. 2 is a schematic circuit diagram of the embodiment of FIG. 1.

In FIG. 2, there is shown a detailed schematic circuit diagram of the apparatus 10 of FIG. 1 in which the two different flow conditions are created by a first rotator 26 and a second rotator 28 in the solution container 12 so as to define a differential flow cell 12a. The first rotator 26 is operatively connected to the slow flow electrode SE (anode) and is rotated at a relatively slow speed so as to obtain a slow flow condition. The second rotator 28 is operatively connected to the fast flow electrode FE (cathode) and is rotated at a relatively faster speed so as to obtain a fast flow condition. For example, the slow flow electrode may be rotated at 50 r.p.m. and the fast flow electrode may be rotated at 500 r.p.m.

It will be noted that a Luggin capillary 30 is connected between the slow flow electrode SE and the reference electrode RE so as to decrease the solution ohmic drop in the measurements which are obtained by the device 22. Further, if needed, in order to provide a realistic simulation of the localized corrosion phenomena commonly found in cooling water systems, an air bubbler 32 may be used to bubble oxygen into the liquid 14 so as to obtain an aerated environment. The shaded portions on the respective slow flow, fast flow; and auxiliary electrodes are used to indicate the relative surface areas thereof. In other words, the fast flow electrode FE is approximately ten times larger in surface area than the slow flow electrode SE.

In FIG. 3, there is illustrated in a diagrammatical representation of an alternate method of creating a differential flow cell 12b. As can be seen, there are provided two parallel flow channels 34 and 36 which are connected together by a common feed flow channel 38. The electrolytic liquid 14 enters through a flow inlet channel 40. The slow flow electrode SE is disposed in the slow flow channel 34, and the fast flow electrode FE is disposed in the fast flow channel 36. The reference electrode RE and the auxiliary electrode AE are disposed also within the flow channel 34. A first flow outlet channel 42 is connected to the flow channel 36 to provide a fast flow condition. A second flow outlet channel 44 is connected to the flow channel 34, and a flow regulator 46 is placed within the outlet channel 44 so as to control the flow rate therein so as to be less than the flow rate at the first flow outlet channel 42.

In FIG. 4, there is illustrated in a diagrammatical representation of another alternate method of creating a differential flow cell 12c. As can be seen, there are provided two flow chambers 48 and 50 of different cross-sectional areas which are connected in series. The first flow chamber 48 has a larger cross-sectional area than the second flow chamber 50 and thus creates a slow flow condition. One end of the first or slow flow channel 48 is connected to a flow inlet channel 52 for receiving the electrolytic liquid. The other end of the first flow chamber 48 is connected to one end of the second or fast flow chamber 50. The other end of the second flow chamber 50 is connected to a flow outlet channel 54. The slow flow electrode SE, auxiliary electrode AE, and reference electrode RE are disposed within the slow flow chamber 48, and the fast flow electrode FE is disposed within the fast flow chamber 50.

From the foregoing detailed description, it can thus be seen that the present invention provides a method and apparatus for measuring underdeposit corrosion rate or metal corrosion rate under tubercles in cooling water systems. Slow flow and fast flow electrodes are immersed in an electrolytic liquid. Different fluid dynamic conditions are created on the slow flow and fast flow electrodes. Three (3) techniques have been described for performing measurements on a differential flow cell so as to determine the underdeposit localized corrosion rate due to differential flow conditions.

While there has been illustrated and described what are at present considered to be preferred embodiments of the present invention, it will be understood by those skilled in the art that various changes and modifications may be made, and equivalents may be substituted for elements thereof without departing from the true scope of the invention. In addition, many modifications may be made to adapt a particular situation or material to the teachings of the invention without departing from the central scope thereof. Therefore, it is intended that this invention not be limited to the particular embodiments disclosed as the best modes contemplated for carrying out the invention, but that the invention will include all embodiments falling within the scope of the appended claims.

What is claimed is:

1. A method for measuring underdeposit localized corrosion rate of a metal structure under differential flow conditions encountered in actual cooling water systems, said method comprising the steps of:
   providing a first electrode defining a slow flow electrode;
   providing a second electrode defining a fast flow electrode;
   said slow flow and said fast flow electrodes being made of the same material as said metal structure;
   immersing said slow flow and fast flow electrodes in an electrolytic liquid;
   creating different fluid dynamic conditions on said slow flow and fast flow electrodes; and
   extrapolating the anodic branches of the polarization curves of said slow flow and fast flow electrodes to a corrosion potential to determine the underdeposit localized corrosion rate due to differential flow conditions.

2. A method as claimed in claim 1, wherein the step of extrapolating includes the step of plotting the values of the current obtained at the slow flow electrode as a function of voltage to produce a first curve.

3. A method as claimed in claim 2, wherein the step of extrapolating includes the step of plotting the values of the current obtained at the fast flow electrode as a function of voltage to provide a second curve.

4. A method as claimed in claim 3, wherein the step of extrapolating includes the step of linearizing the first curve to produce a first line and intersecting said corrosion potential with said first line to obtain the underdeposit localized corrosion rate.

5. A method as claimed in claim 1, wherein the step of creating the different fluid dynamic conditions includes the step of rotating said slow flow electrode at a first speed to provide a slow flow condition and rotating said fast flow electrode at a second speed which is higher than the first speed so as to provide a fast flow condition.

6. A method as claimed in claim 1, wherein the step of creating the different fluid dynamic conditions includes the steps of placing said slow flow electrode in a first of two parallel flow channels, placing said fast flow electrode in a second of two parallel flow channels, and regulating the flow rate in said first of two parallel flow channels to be slower than in said second of two parallelflow channels.

7. A method as claimed in claim 1, wherein the step of creating the different fluid dynamic conditions includes the steps of placing said slow flow electrode in a first of two series-connected flow chambers, placing said fast flow electrode in a second of two series-connected flow chambers, and forming said first of two series-connected flow chambers to have a cross-sectional area to be larger than in said second of two series-connected flow chambers.

8. A method as claimed in claim 1, wherein said slow flow electrode is made of a smaller surface area than said fast flow electrode.

9. An apparatus for measuring underdeposit localized corrosion rate of a metal structure under differential flow conditions encountered in actual cooling water systems, said apparatus comprising:

a slow flow electrode adapted to be disposed in an electrolytic liquid;

a fast flow electrode adapted to be disposed in the electrolytic liquid;

said slow flow and said fast flow electrodes being made of the same material as said metal structure;

means for creating different fluid dynamic conditions on said slow flow and fast flow electrodes;

an ammeter connected between said slow flow and fast flow electrodes for measuring the current flowing therebetween;

means for measuring a current flowing between said slow flow electrode separately and an auxiliary electrode adapted to be immersed in said electrolytic liquid to determine a first polarization resistance; and said current flowing between said slow flow and fast flow electrodes and said first polarization resistance being used to determine the underdeposit localized corrosion rate due to differential flow conditions.

10. An apparatus as claimed in claim 9, further including a reference electrode adapted to be immersed in said electrolytic liquid and wherein said means for measuring the current is connected between said slow flow electrode and said auxiliary electrode to determine the first polarization resistance.

11. An apparatus as claimed in claim 9, wherein said means for creating the different fluid dynamic conditions includes means for rotating said slow flow electrode at a first speed to provide a slow flow condition and means for rotating said fast flow electrode at a second speed which is higher than the first speed so as to provide a fast flow condition.

12. An apparatus as claimed in claim 9, wherein said means for creating the different fluid dynamic conditions includes means for placing said slow flow electrode in a first of two parallel flow channels, means for placing said fast flow electrode in a second of two parallel flow channels, and means for regulating the flow rate in said first of two parallel flow channels to be slower than in said second of two parallel flow channels.

13. An apparatus as claimed in claim 9, wherein said means for creating, the different fluid dynamic conditions includes means for placing said slow flow electrode in a first of two series-connected flow chambers, means for placing said fast flow electrode in a second of two series-connected flow chambers, said first of two series-connected flow chambers having a cross-sectional area larger than that of said second of said two series-connected flow chambers.

14. An apparatus as claimed in claim 9, wherein said flow flow electrode is made of a smaller surface area than said fast flow electrode.

15. An apparatus for measuring underdeposit localized corrosion rate of a metal structure under differential flow conditions encountered in actual cooling water systems, said apparatus comprising:

a slow flow electrode adapted to be disposed in an electrolytic liquid;

a fast flow electrode adapted to be disposed in the electrolytic liquid;

said slow flow and said fast flow electrodes being made of the same material as said metal structure;

means for creating different fluid dynamic conditions on said slow flow and fast flow electrodes;

means for shorting said slow and fast flow electrodes together and for measuring a current flowing between the shorted slow and fast flow electrodes and an auxiliary electrode adapted to be immersed in said electrolytic liquid to determine a first polarization resistance;

means for measuring a current flowing between said fast flow electrode separately and the auxiliary electrode to determine a second polarization resistance; and means for producing a third polarization resistance associated with said slow flow electrode based upon said first and second polarization resistances which is used to determine the underdeposit localized corrosion rate due to differential flow conditions.

16. An apparatus as claimed in claim 15, further including a reference electrode adapted to be immersed in said electrolytic liquid and wherein said means for measuring the current is connected between said fast flow electrode and said auxiliary electrode to determine the second polarization resistance.

17. A method for measuring underdeposit localized corrosion rate of a metal structure under differential flow conditions encountered in actual cooling water systems, said method comprising the steps of:

providing a first electrode defining a slow flow electrode;

providing a second electrode defining a fastflow electrode;

said slow flow and said fast flow electrodes being made of the same material as said metal structure;

immersing said slow flow and fast flow electrodes in an electrolytic liquid;

creating different fluid dynamic conditions on said slow flow and fast flow electrodes;

measuring a current flowing between said slow flow and fast flow electrodes;

measuring a current flowing between said slow flow electrode separately and an auxiliary electrode to determine a first polarization resistance; and utilizing said current flowing between said slow flow and fast flow electrodes and said first polarization resistance to determine the underdeposit localized corrosion rate due to differential flow conditions.

18. A method for measuring underdeposit localized corrosion rate of a metal structure under differential flow conditions encountered in actual cooling water systems, said method comprising the steps of:

providing a first electrode defining a slow flow electrode;

providing a second electrode defining a fast flow electrode;

said slow flow and said fast flow electrodes being made of the same material as said metal structure;

immersing said slow flow and fast flow electrodes in an electrolytic liquid;

creating different fluid dynamic conditions on said slow flow and fast flow electrodes;

shorting said slow and fast flow electrodes together and measuring a current flowing between the shorted slow and fast flow electrodes and an auxiliary electrode to determine a first polarization resistance;

measuring a current flowing between said fast flow electrode separately and the auxiliary electrode to determine a second polarization resistance; and utilizing said first and second polarization resistances to produce a third polarization resistance associated with said slow flow electrode which is used to determine the underdeposit localized corrosion rate due to differential flow conditions.

* * * * *

UNITED STATES PATENT AND TRADEMARK OFFICE
CERTIFICATE OF CORRECTION

PATENT NO. : 5,275,704
DATED : JANUARY 4, 1994
INVENTOR(S) : BO YANG

It is certified that error appears in the above-indentified patent and that said Letters Patent is hereby corrected as shown below:

Column 11, line 52, (claim 14, line 2);

flow flow electrode is made of a smaller surface area

LETTERS PATENT SHOULD READ AS:

slow flow electrode is made of a smaller surface area

Signed and Sealed this

Seventeenth Day of May, 1994

Attest:

BRUCE LEHMAN

*Attesting Officer*  *Commissioner of Patents and Trademarks*